United States Patent [19]

Günter

[11] Patent Number: 4,675,180

[45] Date of Patent: Jun. 23, 1987

[54] PROCESS FOR PREPARING QUATERNARY AMMONIUM SALTS

[75] Inventor: Franz Günter, Riehen, Switzerland

[73] Assignee: Ciba-Geigy Corporation, Ardsley, N.Y.

[21] Appl. No.: 830,434

[22] Filed: Feb. 18, 1986

Related U.S. Application Data

[63] Continuation of Ser. No. 505,649, Jun. 20, 1983, abandoned.

[30] Foreign Application Priority Data

Jul. 5, 1982 [CH] Switzerland .......................... 4084/82
Jan. 25, 1983 [CH] Switzerland ............................ 396/83

[51] Int. Cl.$^4$ ......................... A61K 7/06; C07C 91/26
[52] U.S. Cl. ........................................ 424/70; 564/292
[58] Field of Search .................... 564/292; 424/70, 71; 71/121

[56] References Cited

U.S. PATENT DOCUMENTS

| | | | |
|---|---|---|---|
| 2,127,476 | 8/1938 | Ulrich et al. | 564/292 |
| 2,137,314 | 11/1938 | Ulrich et al. | 564/292 |
| 2,173,069 | 9/1939 | Ulrich et al. | 564/292 |
| 3,155,591 | 11/1964 | Hilfer | 424/70 |
| 3,482,961 | 12/1969 | Nickell et al. | 71/121 |
| 3,698,452 | 10/1972 | Olson et al. | 424/70 |
| 3,876,760 | 4/1975 | Nersesian et al. | 424/70 |
| 4,061,150 | 12/1977 | Dasher et al. | 424/71 |
| 4,165,369 | 8/1979 | Watanabe et al. | 424/70 |
| 4,421,932 | 12/1983 | Rutyen et al. | 564/292 |

FOREIGN PATENT DOCUMENTS 4226189 12/1966 Japan .................................. 564/292

Primary Examiner—James H. Reamer
Attorney, Agent, or Firm—Edward McC. Roberts

[57] ABSTRACT

Compounds of the formula

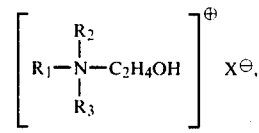

in which $R_1$ is long-chain alkyl, $R_2$ and $R_3$ are each lower alkyl and $X^\ominus$ is an anion, are prepared by quaternizing amines of the formula $R_1R_2R_3N$ with ethylene oxide in the presence of acid. This gives the quaternary compounds in virtually quantitative yield. The compounds are particularly suitable for use in hair cosmetics.

3 Claims, No Drawings

PROCESS FOR PREPARING QUATERNARY AMMONIUM SALTS

This is a continuation of application Ser. No. 505,649 filed on June 20, 1983 now abandoned.

The present invention relates to a process for preparing quaternary ammonium salts.

According to DE No. 646,339 quaternary ammonium bases can be prepared by reacting tertiary amines with ethylene oxide in the presence of water. In this process, it may be necessary to use an excess of ethylene oxide to obtain substantial conversion of the amine into the corresponding ammonium base. According to DE No. 2,052,321 quaternary ammonium bases are prepared at elevated temperatures and under pressure by reacting primary or secondary amines with ethylene oxide in the presence of water. The bases obtained (ammonium hydroxides) can then be reacted with acids to give the corresponding quaternary ammonium salts.

However, in addition to the desired ammonium compounds said processes also produce large amounts of undesirable by-products. As described in DE No. 646,339, for example, the resulting quaternary bases can react with further amounts of ethylene oxide to give condensation products. This is particularly the case when ethylene oxide is used in excess. In the process disclosed in DE No. 2,052,321, the starting compounds themselves can add ethylene oxide to give tertiary amine/ethylene oxide adducts. The formation of such by-products is a great disadvantage, since not only does it reduce the yield of desirable reaction products but generally also necessitates extensive working-up to arrive at pure end products.

It is therefore an object of the present invention to provide a process for preparing quaternary ammonium salts in high purity and yield.

This object is achieved by quaternising tertiary amines in an aqueous medium in the presence of acid with ethylene oxide.

The present invention thus provides a process for preparing compounds of the formula

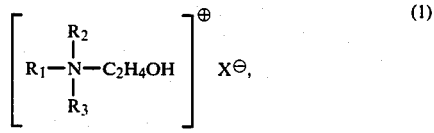

in which $R_1$ is alkyl having 8 to 22 carbon atoms, $R_2$ and $R_3$ are each alkyl having 1 to 4 carbon atoms and $X^\ominus$ is an anion, which comprises quaternising a compound of the formula

in which $R_1$, $R_2$ and $R_3$ are as defined above, in an aqueous medium adjusted to a pH-value of 7.5-9 by means of an acid, with ethylene oxide at room temperature or elevated temperatures and under atmospheric or superatmospheric pressure, adjusting the reaction mixture to a pH-range of 3-7 by adding more of the same acid, and, optionally, isolating the resulting ammonium salt.

The invention also relates to the compounds, in particular the phosphates, obtained in this process, to their use in hair cosmetics and to aqueous or aqueous-alcoholic solutions of these compounds.

The radicals $R_1$, $R_2$ and $R_3$ in the compounds of the formula (1) are alkyl. $R_2$ and $R_3$ are each preferably alkyl having 1 to 4 carbon atoms, for example methyl, ethyl, propyl or butyl, methyl being particularly preferred. $R_1$ is preferably alkyl having 8 to 22 carbon atoms, for example octyl, nonyl, decyl, dodecyl, hexadecyl, ocatadecyl, eicosyl or docosyl. Straight-chain alkyl radicals are preferred. Alkyl radicals having 10 to 16 carbon atoms are particularly suitable, hexadecyl being of particular importance.

Candidates for use as acids in the quaternisation of amines of the formula (2) by means of ethylene oxide are inorganic acids, for example hydrochloric acid, hydrobromic acid, sulfuric acid, phosphoric acid, or nitric acid, and organic acids, for example low molecular weight mono-, di- or tri-carboxylic acids having, for example 1 to 6, preferably 1 to 4, carbon atoms, such as formic acid, acetic acid, glycolic acid, oxalic acid, lactic acid or citric acid. Accordingly $X^\ominus$ is, for example, chloride, bromide, sulfate, hydrogensulfate, hydrogenphosphate, dihydrogenphosphate, nitrate, formate, acetate, glycolate, oxalate, lactate or citrate. Phosphoric acid is particularly suitable.

Room temperature is to be understood as meaning the temperature range from about 15 to 30° C. This definition considers climatic conditions differing with geographic latitude. Elevated temperatures is to be understood as meaning the temperature range which extends from room temperature to about 90° C. The quaternisation is preferably carried out at 60° to 80° C.

The process of the invention can be significantly speeded up by applying pressure. Suitable pressures are approximately within the range from 0.5 to 1.5 bar gauge.

The presence of a certain amount of acid in the quaternisation of tertiary amines using ethylene oxide is a fundamental prerequisite for virtually quantitative, i.e. greater than 95%, conversion of initial amine, because if no acid is added, only about ⅔ of initial amine is quaternised. This degree of conversion cannot even be increased by using a 100% excess of ethylene oxide. Moreover, in the absence of acid the viscosity of the reaction mixture rises very rapidly as ethylene oxide is passed in. A waxy mass forms towards the end of the reaction, i.e. after about ⅔ of the conversion, and cannot be stirred or pumped. In the presence of acid, however, the quaternisation of the amine proceeds almost quantitatively to give a clear, easily pourable aqueous solution of the quaternary ammonium base.

An amount of acid is suitable if it makes the reaction solution weakly alkaline before any ethylene oxide is passed in. The pH-value is preferably within the range from 7.5 to 9. After the reaction has ended, the same acid is then used to convert the ammonium base obtained into the corresponding ammonium salt. As more acid is added, the pH-value of the solution shifts into the neutral to weakly acid range and preferably assumes a value of 3 to 7. If all the acid were already present in the quaternisation, hydrolysis products or ester compounds of ethylene oxide could easily form, while quaternising ammonium compounds would only be produced in low concentrations.

The compounds prepared according to the invention are generally not isolated, but are used in the form of the aqueous solutions obtained at the end of the preparation.

The compounds prepared according to the invention are suitable, for example, for use in hair cosmetics, in particular in hairconditioning agents.

Preparing these agents from the compounds prepared according to the invention presents no problem, since these compounds, not only in water but also in, for example, water/alcohol mixtures, give clear, stable solutions which simplify the treatment of hair. Aqueous solutions of this type can contain 0.1 to 1, preferably 0.2 to 0.5, % by weight of compounds prepared according to the invention. Alcohol, preferably ethanol or i-propanol, can be added to the aqueous solutions in amounts of 10 to 50, preferably 20 to 30% by weight. These solutions, solutions which contain compounds prepared according to the invention, simplify in particular the final rinse of hair. The compounds are also suitable for use in compositions for, for example, setting permanent waves, and they also help to keep the styled hair in shape. The ammonium salts are resistant to oxidising agents, for example, hydrogen peroxide (preferably solutions having a pH-value of about 2.5) or sodium bromate (preferably solutions having a pH-value of about 7.9), so that the ammonium salts' good conditioning effects even endure when, for example, the hair is oxidatively dyed.

The following Examples illustrate the invention without in any way restricting the scope thereof. Parts and percentages are by weight, unless otherwise stated.

EXAMPLE 1

0.5 mol of dimethylhexadecylamine is introduced into 440 ml of distilled water. Adding 0.2 mol of 75% phosphoric acid gives a clear solution, which is heated to 75° to 80° C. 0.75 ml of ethylene oxide is then passed in over 60 minutes. The heating is then removed and a further 0.2 mol of 75% phosphoric acid and 23 ml of distilled water are added. The reaction mixture is then filtered, if necessary, to give 665 to 670 g of a clear aqueous solution which contains about 30% of the ammonium salt of the formula

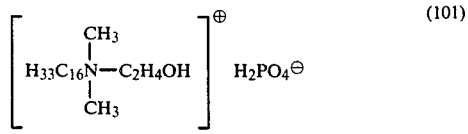

(101)

This corresponds to a yield of 96 to 97% of compound of the formula (101).

Application of superatmospheric pressure increases the rate of ethylene oxide uptake. If the pressure is about 0.5 bar gauge, the ethylene uptake is complete after 20 minutes, while under about 1.5 bar gauge the uptake is complete after only 12 minutes. The yields of compounds of the formula (101) are also almost quantitative.

The solutions obtained can be used in hair cosmetics, either directly (as a 30% solution) or in a dilute form.

The compounds of the formula (101) can be obtained from the aqueous solutions in a solid form, for example by freezing-out or spraydrying.

EXAMPLE 2

0.25 mol of 25% sulfuric acid is added to 0.5 mol of dimethylhexadecylamine in 440 ml of distilled water. The resulting emulsion is heated to 75° C. The heat supply is then removed and 0.7 mol of ethylene oxide is passed into the emulsion in the course of 90 minutes. A pH-value between 9 and 10 is maintained by the simultaneous dropwise addition of 25% sulfuric acid. When the ethylene oxide has been passed in, sulfuric acid is used to adjust a pH-value of 5. This gives 700 to 710 g of an aqueous slightly turbid solution which contains about 30% of the ammonium salt of the formula

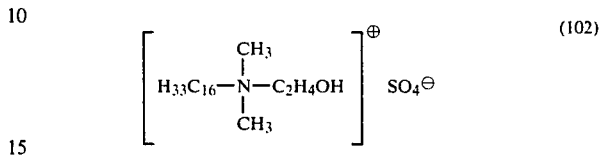

(102)

The above procedure is repeated using dimethylhexadecylamine and sulfuric acid in an equimolar ratio (for example 0.5 mol of amine and 0.5 mol of sulfuric acid). The ammonium salt of the formula

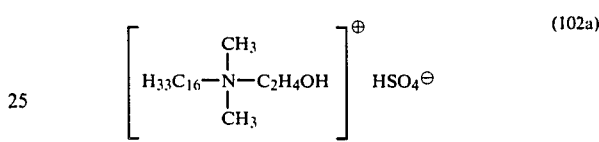

(102a)

is obtained as an approximately 30% solution at pH 1.5–2.

EXAMPLE 3

A solution of 0.25 mol of d,1-lactic acid in 22.5 ml of distilled water is added to 0.5 mol of dimethylhexadecylamine in 400 ml of distilled water. The resulting white emulsion is heated to 75° C. 0.75 mol of ethylene oxide is then passed in over 2 to 3 hours, while, at the same time, a solution of 0.25 mol of d,1-lactic acid in 22.5 ml of distilled water is added dropwise at such a rate that the pH-value of the emulsion is always 9 to 10. Since the viscosity of the reaction mass increases towards the end of the reaction, the temperature is raised to 90 to 92° C. to ensure efficient stirring. When the ethylene oxide has been passed in, the resulting, still warm mobile solution is brought to a pH-value of 4.5–5 by means of the lactic acid solution.

This gives 690 to 700 g of a clear aqueous solution which contains about 30% of the ammonium salt of the formula

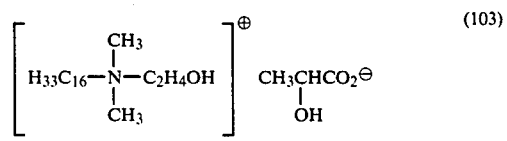

(103)

and solidifies on cooling into a clear gel.

EXAMPLE 4

A solution of 0.08 mol of citric acid (monohydrate) in 32 ml of distilled water is added to 0.5 mol of dimethylhexadecylamine in 355 ml of distilled water. The resulting white emulsion is heated to 75° C. 0.75 mol of ethylene oxide is then passed in over 2 hours, during which the reaction mass is held at a pH-value of 9–10 by the dropwise addition of a further solution of 0.08 mol of citric acid (monohydrate) in 32 ml of distilled water. When the ethylene oxide has been passed in, more citric acid (0.05 mol dissolved in 15 ml of distilled water) is added to adjust the reaction mass of a pH-value of 5.5.

This gives 645 to 655 g of a clear aqueous solution which contains about 30% of the ammonium salt of the formula

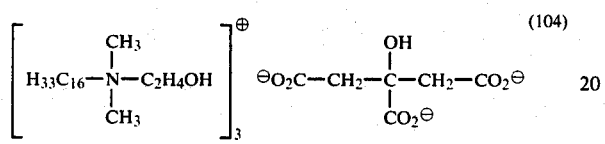
(104)

Carrying out the reaction with a total of 0.5 mol of citric acid gives a likewise clear solution of the ammonium salt of the formula

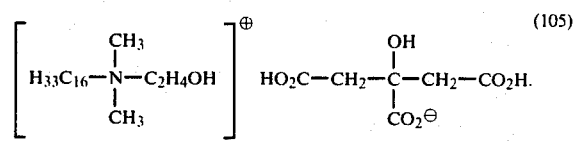
(105)

What is claimed is:

1. A compound of the formula

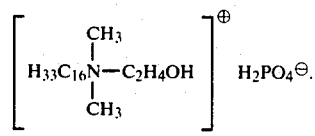

2. An aqueous or aqueous-alcoholic solution of the compound of the formula

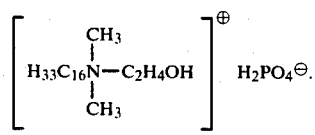

3. A method of conditioning hair which comprises applying to the hair the aqueous or aqueous-alcoholic solution according to claim 2.

* * * * *